United States Patent [19]
Park et al.

[11] Patent Number: 5,466,829
[45] Date of Patent: Nov. 14, 1995

[54] NEW GINKGOLIDE DERIVATIVES AND A PROCESS FOR PREPARING THEM

[75] Inventors: Hwa K. Park; Suk K. Lee, both of Kyonggi; Pyeong U. Park, Seoul; Wie J. Kwan, both of Seoul, all of Rep. of Korea

[73] Assignee: Sunkyong Industries Co., Ltd., Rep. of Korea

[21] Appl. No.: 204,169

[22] PCT Filed: Sep. 18, 1992

[86] PCT No.: PCT/KR92/00043

§ 371 Date: Jul. 5, 1994

§ 102(e) Date: Jul. 5, 1994

[87] PCT Pub. No.: WO93/06107

PCT Pub. Date: Apr. 1, 1993

[30] Foreign Application Priority Data

Sep. 18, 1991 [KR] Rep. of Korea ............... 91-16260
Oct. 17, 1991 [KR] Rep. of Korea ............... 91-18268

[51] Int. Cl.$^6$ ............... C07D 313/06; C07D 307/93; C07D 493/22
[52] U.S. Cl. ............... 549/297; 549/348
[58] Field of Search ............... 549/297, 348

[56] References Cited

U.S. PATENT DOCUMENTS 5,089,636  2/1992  Kwak et al. ............... 549/297

OTHER PUBLICATIONS

Corey et al., "Total Synthesis of Ginkgolide A," *Tetrahedron Letters*, Pergamon Press; Oxford, N.Y.; vol. 29; No. 25, pp. 3205–3206 (1988).

Corey et al., "Simple Analogs of Ginkgolide B Which Are Highly Active Antagonists Of Platelet Activating Factor" *Tetrahedron Letters*, Pergamon Press; Oxford, N.Y.; vol. 30; No. 49, pp. 6959–6962 (1989).

Chemical Abstracts, vol. 110, No. 15 (1989), 134,946m.
Chemical Abstracts, vol. 113, No. 9 (1990), 78,720f.
Weinges et al., "Chemistry Of Ginkgolides, II [1].–Isolation And Structural Elucidation Of A New Ginkgolide", Liebigs Ann. Chem., vol. 5, pp. 522–526 (English Translation), 1987.

*Primary Examiner*—C. Warren Ivy
*Assistant Examiner*—Ba K. Trinh
*Attorney, Agent, or Firm*—Kenyon & Kenyon

[57] ABSTRACT

The present invention relates to new ginkgolide derivatives of the formula (I) as below which represents PAF-antagonistic activity and the method for the preparation thereof, by that the cyclic compounds of substituted Ginkgolide B derivatives are produced by reacting the known Ginkgolide B and C mixture having the hydroxy group in 1- and 10-carbon with acid, then they are separated, and separated Ginkgolide B derivatives is hydrolyzed in acidic aqueous solution. And the present invention is related to make use it as PAF-antagonistic agent through separating the only one component of the new ginkgolide derivative by those methods.

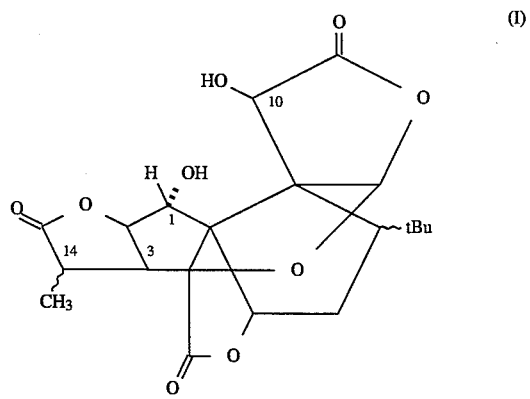

6 Claims, No Drawings

NEW GINKGOLIDE DERIVATIVES AND A PROCESS FOR PREPARING THEM

This application is filed under 35 USC 371 of PCT/KR92/00043, filed Sep. 18, 1992.

TECHNICAL FIELD

The present invention relates to new ginkgolide derivative, having valuable PAF-antagonistic activity, of formula (I) as below and a process for preparing them, especially a process for preparing Ginkgolide B derivatives by separating only one component of ginkgolide, not mixture.

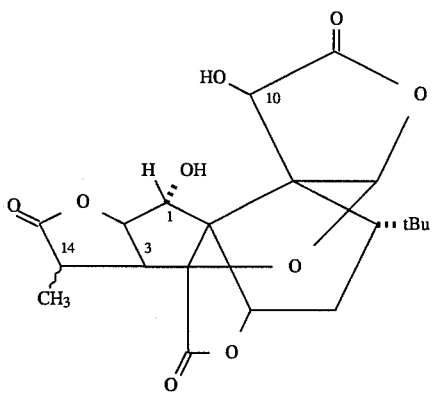

BACKGROUND ART

The ginkolides, a terpenoid compounds, from the roots and leaves of the Ginkgo tree are the substances having very characteristic chemical structure. Among ginkgolides being isolated from the natural substance by Nakanishi in 1967, 4 kinds of ginkgolide were determined and named the Ginkgolide A, B, C and M by characteristic of its chemical structure, and after the Ginkgolide J was identified by Weing in 1987. General chemical structure of these ginkgolides are the formula A as below.

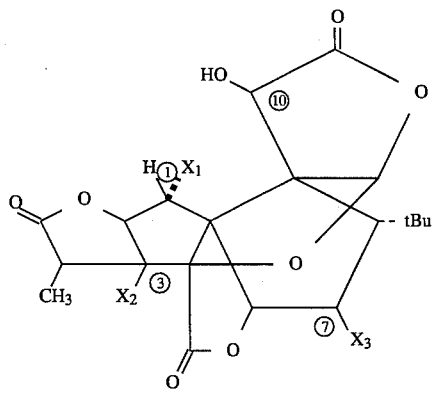

in which
$X_1$, $X_2$, and $X_3$ are hydrogen or hydroxy of the same or not.

The above ginkgolides of the formula A are indicated in the following Table 1 as below by way of substituent $X_1$, $X_2$, and $X_3$.

TABLE 1

| Ginkgolide | $X_1$ | $X_2$ | $X_3$ |
|---|---|---|---|
| A | H | OH | H |
| B | OH | OH | H |
| C | OH | OH | OH |
| M | OH | H | OH |
| J | H | OH | OH |

Especially, the studies about them are going on progress, becauce it has been found recently that ginkgolides have PAF-antagonistic activity.

Meanwhile, Barquet of Institute of Henri Beaufour Company in France synthesized new derivatives that substituted hydroxy group in 1- and 10-carbon of the ginkgolide structure with methoxy or ethoxy group by treating the ginkgolide with diazoalkane. (Brit. pat. appl. 2,211,841)

It is well known that these ginkgolides are distinguished from the difference of having or not hydroxy group in 1, 3, and 7-carbon in its chemical structure, but it is very difficult to separate them into each substance because of very similar chemical properties.

Therefore, the pure individual substance was separated by passing through silicagel column [K. Nakanish, Pure Appl. Chem. 1967. 89–113] or ion exchange resin such as Cephadex-LH-20 by Weing et al., two or three times, [Liebigs. Ann. Chem, 1987. 521–526] after several times of fractional recrystallization using the difference of the solubility coming from the difference of hydroxy group.

But, these usual methods for separating using the fractional recrystallization have very low efficiency because of similar properties of each component. Especially because the Ginkgolide A and B have similar properties, $R_f$ values for the Ginkgolide A and B by thin layer chromatography(silicagel plate, developing solvent; toluene:acetone= 7:3) is nearly no difference as each 0.32 and 0.30, and so they could not be seperated by passing through silicagel column. So there am much difficulty, e.g. they have a uneconomical defect that repeated it several times or used high price ion exchange resin such as Cephadex-LH-20, for separation.

Moreover, recently the effectiveness of ginkgolides are increasing as time goes on, and it has been found that the activity of the Ginkgolide B among them is superior to compared with another 4 kinds of ginkgolide. But the Ginkgolide A, B, and C mixture is used as a drag [Brit. pat. Appl. 2,162,062A], because the method for effective separation was not developed.

Therefore, it is necessary to separate the pure one component of the Ginkgolide B, because the Ginkgolide A and C have relatively low activity than the Ginkgolide B, and also it is necessary to separate for using characteristics of each component. So if they am separated each component of the ginkgolide with simple, easy and economical, a new field for the utilization of the ginkgolides will open up.

Therefore, we, inventors, perfected the present invention by finding out that it is possible to effectively separate the ginkgolide derivatives into each component by substituting the hydroxy group, availing of the chemical structural difference of each component of the Ginkgolide A, B, and C, as a result of the ceaseless study for new synthesis of the ginkgolides and for overcoming the difficulty for separating them from the mixed component.

SUMMARY OF THE INVENTION

The object of the present invention demonstrate that the new structural ginkgolide derivatives inhibit the aggregation induced by PAF and a process for separating and preparing one component of ginkgolides through the method that changing the difference of polarity of each component by substituting the hydroxy group of the ginkgolides.

DETAILED DESCRIPTION OF THE INVENTION

The present invention relates to the Ginkgolide B derivative of above formula (I). Also, this invention contains the new derivatives of formula (II), (III), and (IV) as below producing as the intermediate in the synthetic route of the Ginkgolide B derivative of above formula (I).

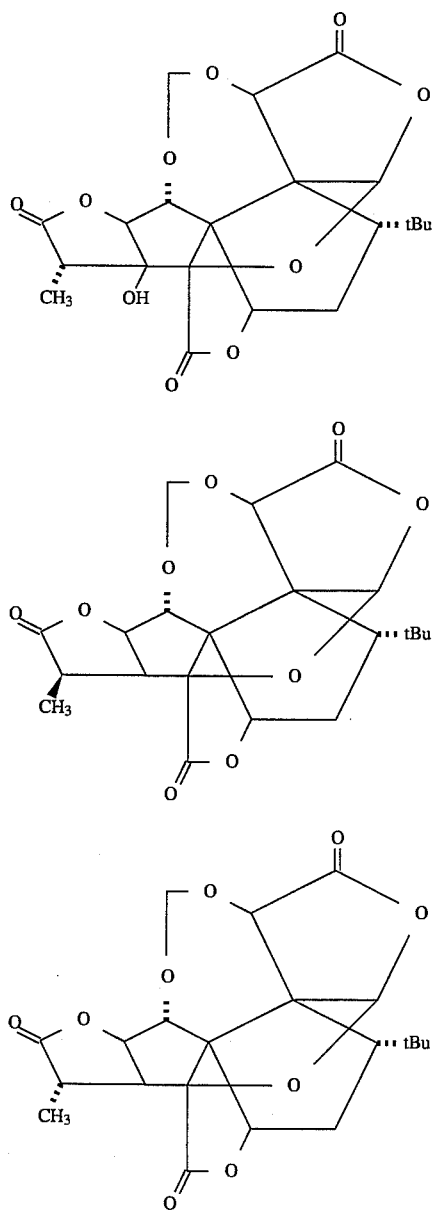

Also, the present invention contains PAF-antagonistic having one or more Ginkgolide B derivatives of above formula (I), (II), (III), and (IV) as an effective component.

The present invention is the process tier preparing the ginkgolide derivatives by that a kind of cyclic compound of above formula (II) is prepared by separation from the unreacted ginkgolides after reacting the hydroxy group in 1- and 10-carbon of the known Ginkgolide B and C mixture of above formula (A) with acid, and the compound of above formula (III) and (IV) which removed hydroxy group in 3-carbon are obtained from (II) by dehydroxylation, and the compound of above formula (I) is prepared from (III) and (IV) by hydrolysis in acidic aqueous solution.

In this invention, each component of the ginkgolides can be effectively separated from the ginkgolide mixture as follows:

Because the ginkgolides having hydroxy group in 1- and 10-carbon such as the Ginkgolide B and C are changed to cyclic acetal or ketal type of above formula (II) and but the Ginkgolide A having no hydroxy group in 1-carbon is not changed, the difference of the polarity is arisen from them. Therefore the Ginkgolide A is easily separated from changed ginkgolide by passing through a cheap silicagel column. Then the substituted Ginkgolide B and C derivative of above formula (II) return to the original the Ginkgolide B and C by hydrolysis in acidic aqueous solution e.g. hydrochloric acid.

In accordance with this invention, the new intermediate, 1,10-dioxy-ginkgolide derivative, of above formula (II) are formed by reacting the Ginkgolide B and C mixture which is dissolved in acetic and sulfuric acid mixture with formaldehyde or p-formaldehyde at room temperature for 3~8 hours or at 70°~90° C. for 1~3 hours.

Because the compound of above formula (II) which is obtained in this way is different from the unreacted Ginkgolide A in polarity, the new intermediate, 1,10-dioxy-ginkgolide derivative, of above formula (II) and the pure Ginkgolide A, was obtained quantitatively by that diluted reaction mixture in 0° C. of water, then extracted with solvent which is not miscible with water being selected from chloroform, ethylacetate, and ether, then dried the layer of organic solvent at reduced pressure, and then passed through silicagel column using chloroform or chloroform-methanol mixture.

The pure Ginkgolide B is obtained by acid hydrolysis of the ginkgolide derivative of above formula (II) that is obtained by above separation, for example, by that added the compound of above formula (II) in acid solution being selected from e. g. 2~4N hydrochloric acid, sulfuric acid or acetic acid, then heated to 90°~120° C. for 2~3 hours, then diluted with 0° C. of water, then extracted fractionally with nonpolar solvent being selected from chloroform, ether, or acetate, then dried the layer of organic solvent at reduced pressure, then recrystalized with ethylalcohol, methylalcohol or their aqueous solution. At the same time the Ginkgolide C is separated by itself, because of being dissolved in alcohol solution, not precipitated.

In here, looking around in more details the process for separating the Ginkgolide B derivative of above formula (I) of this invention, the new Δ3,14-1,10-dioxy- 14-epi-Ginkgolide B derivative of formula (II-a) as below was formed by that the above separated Ginkgolide B derivative of above formula (II) is reacted with thionylchloride in pyridine solvent, and then the new derivative compound of 3-dihydroxy- 1,10-methylenedioxy-14-epi-Ginkgolide B derivative of above formula (III) is obtained quantitatively by reacting formula (II-a) with hydrogen at platinium carbon catalyst.

The compound of formula (III-a) being decomposed lactone group as below is obtained by reacting the compound of above formula (III) at 60°~70° C. for 1~2 hours in alkali solution e.g. sodiumhydroxide, and the new derivative compound of 3-dehydroxy- 1,10-methylenedioxy-14-epi- Ginkgolide B derivative of a bore formula (IV) that the methyl group in 14 position return to original type is obtained by treating formula (III-a) with acid.

The new Ginkgolide B derivative of formula (I) as a mixture of 3-dehydroxy- 14-epi-Ginkgolide B derivative of formula (I-a) and 3-dehydroxy-Ginkgolide B derivative of formula (I-b) is obtained quantitatively by hydrolysis the above prepared compound of above formula (III) and the compound of above formula (IV) at 90°~120° C. for 2~5 hours in 2~5N acid solution e.g. hydrochloric acid.

The process for preparing the new derivative compounds of this invention can be represented by the reaction scheme as follows.

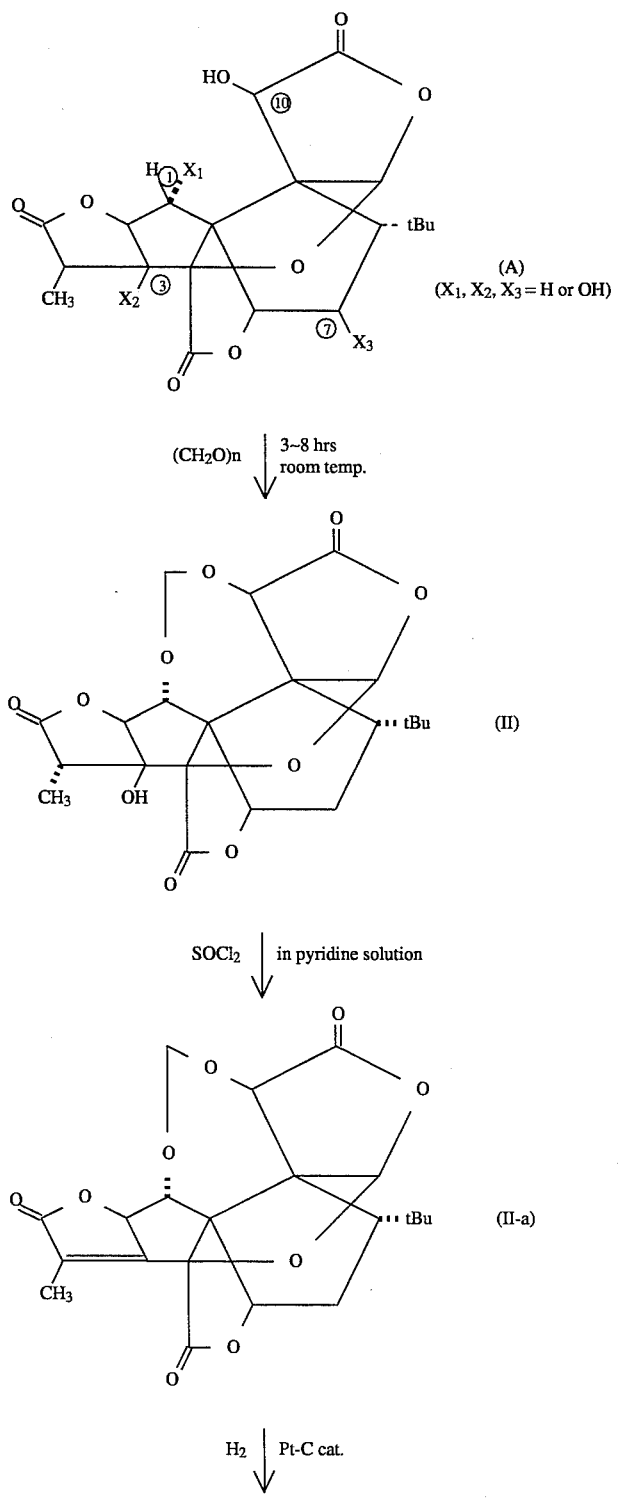

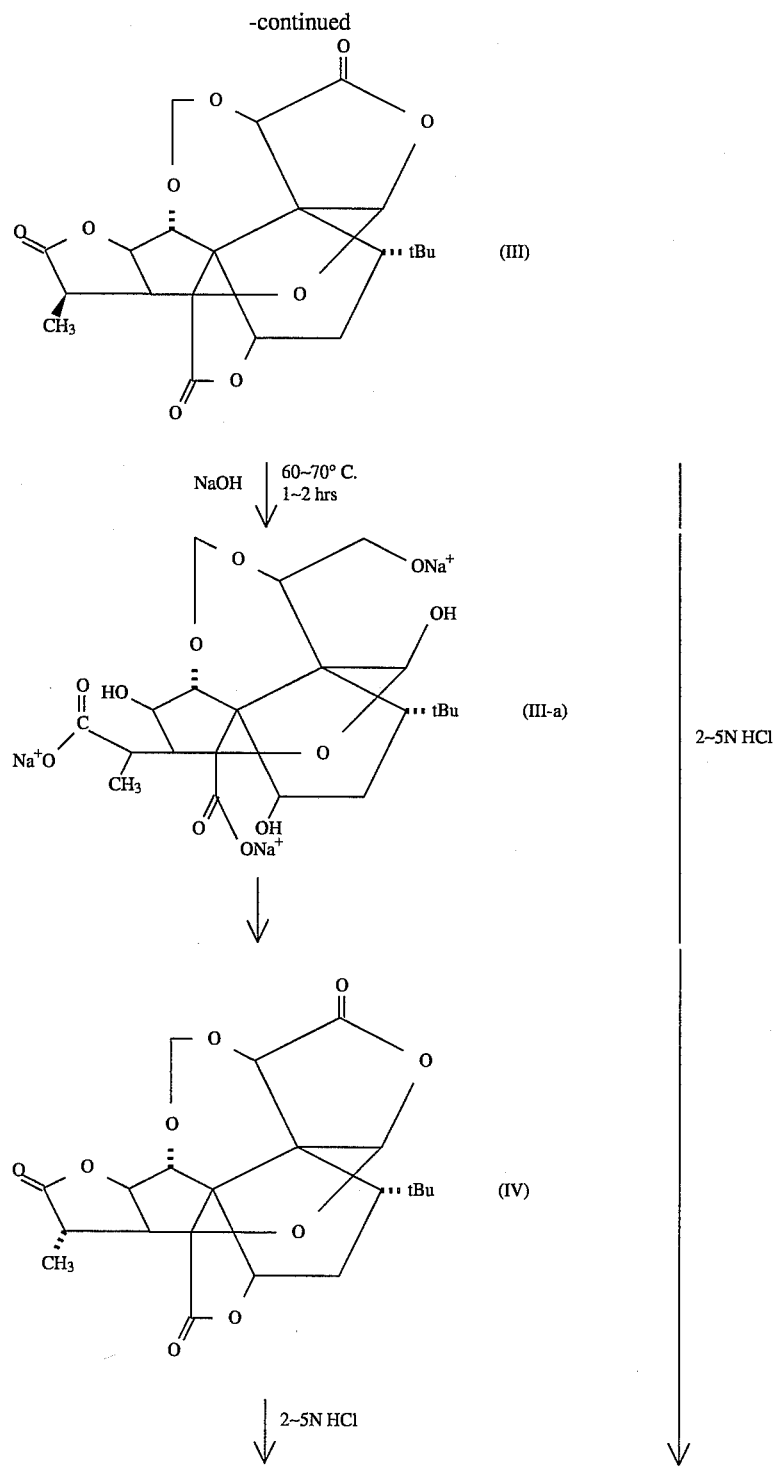

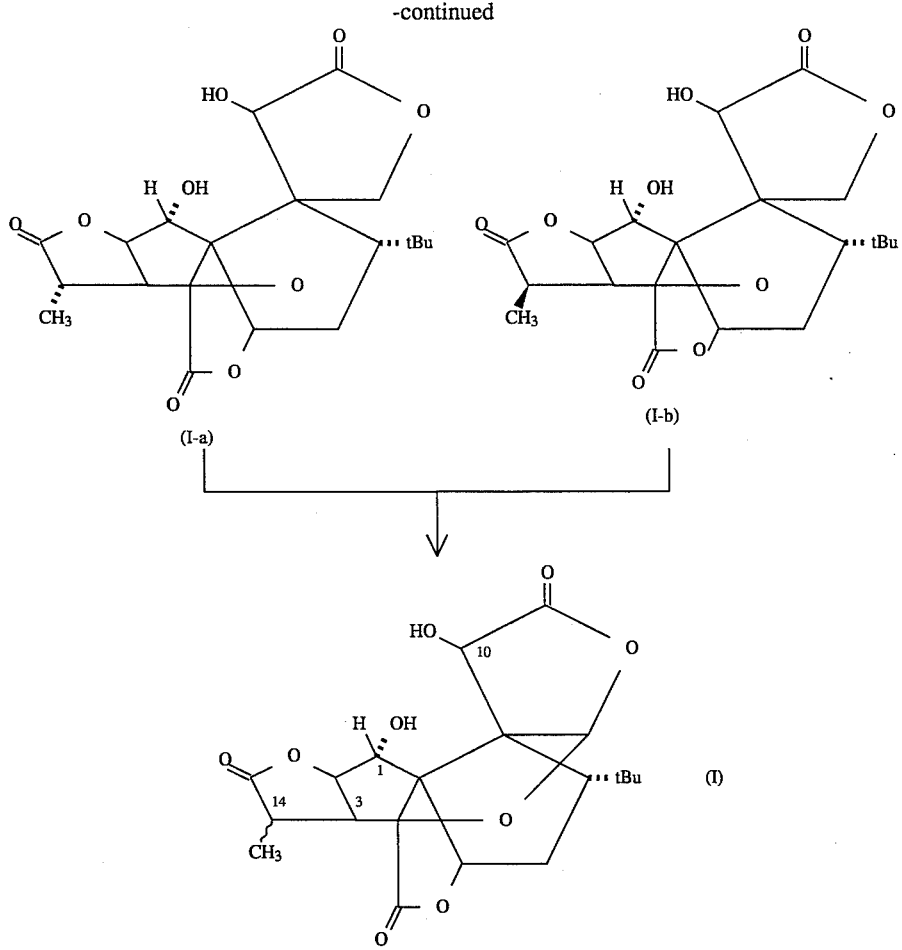

-continued

The new derivative compound of above formula (I) producing as above and formula (II), (III), and (IV) being obtained as the intermediate by the present invention are all the Ginkgolide B derivatives having a similar activity with the original Ginkgolide B.

It is found out that these new derivative compounds have a similar aggregation inhibiting effect for these new derivative compounds is similar to the Ginkgolide A, but low than the original Ginkgolide B, by results of measuring the platelet aggregation inhibiting effect for the new derivative compounds through animal test as the example that mentioned later.

In accordance with this invention, each component of the ginkgolides can be separated effectively and economically from the Ginkgolide A, B, and C mixture. Especially, in the present invention, it is easily separated through changing the hydroxy group in 1- and 10-carbon of the Ginkgolide B and C to cyclic acetal or ketal, but it is respected that the separation can be accomplished easily by the difference of polarity to the Ginkgolide A though changing to cyclic acetal or ketal or similar cyclic type of this.

Because the difference of the polarity is arisen by having or not the hydroxy group of ginkgolides, the method for the separation of ginkgolide by this invention is easy. And because the separated component is recovered by hydrolysis, this method is simple and economic.

In accordance with this invention, through searching the structure-activity relationship of the Ginkgolide B derivatives having hydroxy group in 1, 3, and 10 position, the new Ginkgolide B derivative can be used as PAF-antagonistic agent The following examples more fully illustrate the present invention, but the invention is not intended to be limited thereby.

EXAMPLE 1

Preparation of 1,10-methylenedioxy-Ginkgolide B[formula (II)]

10 g of Ginkgolide B is dissolved in 250 ml of acetic acid and 200 ml of sulfuric acid mixture by heating to 50° C. After adding 20 g of p-formaldehyde, the mixture is stirred at room temperature for 8 hours. The reaction mixture is diluted with 2 l of 0° C. of water and extracted twice with 10 l of dichloromethane. The combined dichloromethane extracts are concentrated by evaporation in a vacuum and recrystallized from 100 ml of ethylalcohol. 9.3 g(90%) of pure 1,10-methylenedioxy-Ginkgolide B is obtained.

$R_f$ values: 0.65[silicagel plate, developing solvent(toluene::acetone=7:3)]

$^1$H-NMR(300 MHz, CDCl$_3$): 5.93(s, 1H); $H_{12}$, 5.36(s, 1H); $H_{10}$, 5.22(brs, 1H); H $H_6$, 5.15(q, 2H); methylene, 4.71(d, 1H); $H_2$, 3.96(d, 1H); $H_1$, 3.07(q, 1H); $H_{14}$, 2.36–2.31(m, 2H); $H_7$, 2.0(dd, 1H); $H_8$, 1.31(d, 3H); Me, 1.10(s, 9H); t-Bu.

Melting point: 380° C. (decomposition)

EXAMPLE 2

10 g of Ginkgolide A and B mixture existing 1:1 by weight is dissolved in 200 ml of acetic acid and 150 ml of sulfuric acid mixture by heating to 50° C. After adding 10 g of p-formalhyde, the mixture is stirred at room temperature for 8 hours. The reaction mixture is diluted with 1.5 l of 0° C. of water and extracted twice with 10 l of chloroform. The combined chloroform extracts are concentrated by evaporation in a vacuum and then 10 g of mixture is obtained. Obtained mixture is passed chloroform and methanol(10:1) mixture through 500 g of silicagel packed column 4.8 g(yield 93%) of pure 1,10-methylenedioxy-Ginkgolide B and 4.7 g(94%) of pure Ginkgolide A are obtained.

Preparation of silicagel packed column 500 g of silicagel(Merck, Cat. No. 9385, 230~400 mesh) is packed in a column(diameter: 5 cm, height: 1.2 m) by pouring chloroform and methanol(10:1) mixed solvent.

EXAMPLE 3

10 g of Ginkgolide A, B and C mixture existing 2:2:1 by weight is dissolved in 200 ml of acetic acid and 150 ml of sulfuric acid mixture by heating to 50° C. After adding 10 g of p-formalhyde, the mixture is stirred at 90° C. for 3 hours. The reaction mixture is diluted with 1.5 l of 0° C. of water and extracted twice with 10 l of ethylacetate. The combined ethylacetate extracts are concentrated by evaporation in a vacuum and then 10 g of mixture is obtained. Obtained mixture is passed through 500 g of silicagel column as the same method as example 2. 3.8 g(yield 92%) of 1,10-methylenedioxy-Ginkgolide B, 3.8 g(95%) of Ginkgolide A, and 1.7 g(85%) of 1,10-methylenedioxy-Ginkgolide C are obtained.

PRODUCED EXAMPLE 4 g of 1,10-methylenedioxy-Ginkgolide B which is obtained above example 1 is stirred with 40 ml of 2N-HCl solution at 100° C. for 3 for 3 hours. The reaction mixture is diluted with 300 ml of water and extracted twice with 200 ml of dichloromethane. The combined dichloromethane extracts are concentrated by evaporation in a vacuum and after dissolving with 30 ml of absolute ethylalcohol at 60° C., stand at 0° C., for 3 hours. The formed precipitation is filtered and then dried under the reduced pressure. 3.7 g(95%) of pure Ginkgolide B is obtained.

EXAMPLE 4

3.8 g of 1,10-methylenedioxy-Ginkgolide B and 1.7 g of 1,10-methylenedioxy-Ginkgolide C which is obtained above example 2 is added in 50 ml of 3-N sulfuric acid and the mixture is stirred at 100° C. for 3 hours. The reaction mixture is cooled to room temperature and diluted with 1.5 l of 0° C. of water and extracted twice with 300 ml of ethylacetate. The combined ethyl acetate extracts are concentrated by evaporation in a vacuum. The evaporation residue is dissolved in 40 ml of anhydrous ethylalcohol by heating to 60° C. The solution is stood at 0° C. for 5 hours and filtered the precipitation and dried. 3.6 g(97%) of pure Ginkgolide B is obtained. The filtrate is concentrated to 1.0 ml. The evaporation residue is dissolved in 20 ml of distilled water. The solution is stood at 0° C. for 2 hours and filtered the precipitation and dried. 1.4 g(83%) of pure Ginkgolide C is obtained.

EXAMPLE 5

Preparation of Δ3,14-1,10-methylenedioxy-Ginkgolide B[formula (II-a)]

10 g of 1,10-methylenedioxy-Ginkgolide B which is obtained above example 1 is dissolved in 250 ml of pyridine and added slowly dropwise 250 ml of thionylchloride at 0° C. After the mixture is stirred for 2 hours, the reaction mixture is added 1000 ml of distilled water and extracted twice with 500 ml of dichloromethane. The combined dichloromethane extracts am concentrated by evaporation in a vacuum and recrystallized from ethylalcohol. 7.7 g(80%) of Δ3,14-,1,10-methylenedioxy-Ginkgolide B is obtained.

IR: 2978 cm$^{-1}$ (ν OH), 1792 cm$^{-1}$ (ν CO)

$^1$H-NMR(300 MHz, CDCl$_3$): 5.96(s, 1H); H$_{12}$, 5.34(s, 1H); H$_{10}$, 5.28(brs, 1H); H$_6$, 5.18(q, 2H); methylene, 5.12(d, 1H); H$_2$, 3.78(d, 1H); H$_1$, 2.37–2.33(m, 2H); H$_7$, 2.04(dd, 1H); H$_8$, 2.11(d, 3H); Me, 1.12(s, 9H); t-Bu.

Melting point: 247° C.

EXAMPLE 6

Preparation of 3-dihydroxy-1,10-methylenedioxy-14-epi-Ginkgolide B[formula (III)]

5 g of Δ3,14-1,10-methylenedioxy-Ginkgolide B which is obtained above example 5 is dissolved in 300 ml of absolute ethylalcohol and added 0.5 g of 10% platinium carbon catalyst. After the mixture is reacted at 60° C. for 2 hours under a hydrogen pressure of about 60 psi, the reaction mixture is filtered for removing catalyst.

The filtrate is concentrated by evaporation in a vacuum. 5 g(97%) of Δ3-dehydroxy- 1,10-methylenedioxy- 14-epi-Ginkgolide B is obtained.

IR: 2963 cm$^{-1}$ (ν OH), 1786 cm$^{-1}$ (ν CO)

$^1$H-NMR(300 MHz, CF$_3$COOD): 6.20(s, 1H); H$_{12}$, 5.73(s, 1H); H$_{10}$, 5.45(d, 1H); H$_{methylene}$, 5.40(S, 1H); H$_6$, 5.25(t, 1H); H$_2$, 5.16(d, 1H); H$_{methylene}$, 4.34(d, 1H); H$_1$, 3.5–3.2(m, 2H); H$_{3,14}$, 2.47(d, 2H); H$_7$, 2.16(t, 1H); H$_8$, 1.70(d, 3H); CH$_3$, 1.20(s, 9H); t-Bu.

Melting point: 234° C.

EXAMPLE 7

Preparation of 3-dehydroxy- 1,10-methylenedioxy-Ginkgolide B[formula (IV)]

5 g of 3-dehydroxy-1,10-methylenedioxy-14-epi-Ginkgolide B which is obtained above example 6 is stirred with 100 ml of 2N-NaOH solution at 60° C. for 2 hours. The reaction mixture is cooled and neutralized with conc-HCl the pH to 2~3. The formed precipitation is filtered and dried and recrystallized from ethylalcohol. 4.7 g(94%) of 3-dihydroxy-1,10-methylenedioxy-Ginkgolide B is obtained.

IR: 2997 cm$^{-1}$ (ν OH), 1792 cm$^{-1}$ (ν CO)

$^1$H-NMR(300 MHz, CF$_3$COOD): 6.21(s, 1H); H$_{12}$, 5.71(s, 1H); H$_{10}$, 5.40(brs, 1H); H$_6$, 5.38(d, 1H); H$_{methylene}$, 5.17(t, 1H); H$_2$, 5.15(d, 1H); H$_{methylene}$, 4.36(d, 1H); H$_1$, 3.28(m, 1H); H$_4$, 3.13(t, 1H); H$_3$, 2.48(d, 2H); H$_7$, 2.20(t, 1H); H$_8$, 1.47(d, 3H); CH$_3$, 1.21(s, 9H); t-Bu.

Melting point: 275° C.

EXAMPLE 8

Preparation of 3-dehydroxy-14-epi-Ginkgolide B[formula (I-b)]

5 g of 3-dehydroxy-1,10-methylenedioxy-14-epi-Ginkgolide B which is obtained above example 6 is stirred with 50 ml of 2N-HCl solution at 100° C. for 3 hours. The reaction mixture is cooled at room temperature. The reaction mixture is diluted with 200 ml of water and extracted twice with 200 ml of dichloromethane. The combined dichloromethane extracts are concentrated by evaporation in a vacuum and recrystallized from 30 ml of ethylalcohol. 4.7 g(95%) of 3-dehydroxy-14-epi-Ginkgolide B is obtained.

$^1$H-NMR(300 MHz, $CF_3COOD$): 6.18(s, 1H); $H_{12}$, 5.77(s, 1H); $H_6$, 5.43(s, 1H); $H_{10}$, 5.37(s, 1H); $H_2$, 5.12(d, 1H); $H_1$, 3.55(t, 1H); $H_3$, 3.32(m, 1H); $H_{14}$; 2.5–2(m, 3H); $H_{7-8}$, 1.62(d, 3H); $CH_3$, 1.20(s, 9H); t-Bu.

Melting point: 235° C.

EXAMPLE 9

Preparation of 3-dehydroxy-Ginkgolide B[formula (I-a)]

5 g of 3-dehydroxy-1,10-methylenedioxy-Ginkgolide B which is obtained above example 7 is stirred with 50 ml of 2N-HCl solution at 100° C. for 3 hours. The reaction mixture is cooled at room temperature. The reaction mixture is diluted with 200 ml of water and extracted twice with 200 ml of dichloromethane. The combined dichloromethane extracts are concentrated by evaporation in a vacuum and recrystallized from 30 ml of ethylalcohol. 4.7 g(95%) of 3-dihydroxy-Ginkgolide B is obtained.

IR: 3597 $cm^{-1}$ (ν OH), 1769 $cm^{-1}$ (ν CO)

$^1$H-NMR(300 MHz, $CF_3COOD$): 6.29(s, 1H); $H_{12}$, 5.60(s, 1H); $H_6$, 5.49(s, 1H); $H_{10}$, 5.24(t, 1H); $H_2$, 4.68(d, 1H); $H_1$, 3.3–3(m, 2H); $H_{3,14}$, 2.5–2(m, 3H); $H_{7-8}$, 1.48(d, 3H); $CH_3$, 1.23(s, 9H); t-Bu.

Melting point: 187° C.

EXAMPLE

Activity test

The blood gathering in the ear artery of the New Zealand White Rabbit of weight 3~3.5 kg was mixed with 3.8% sodium citrate solution at the ratio of 1:9. After centrifuging for 10 minutes at 1000 rpm, the upper Platelet Rich Plasma(PRP) layer was taken. Again after centrifuging for 10 minutes at 3000 rpm, the upper Platelet Poor Plasma(PPP) was taken.

After measuring the platelet figures of the PRP using the Coulter counter, the platelet figures was adjusted to $3\times10^5/\mu l$ by diluting with PPP.

The ginkgolide derivatives which were obtained from the above example 1 and 5~9 was investigated platelet aggregation inhibiting effect by that 270 μl of PRP and 30 μl of the derivative solution was treated using the Chrono-log aggregometer which the light tansmittance of PPP was fixed to 100% and the light tansmittance of PRP was fixed to 0% and then 30 μl of Platelet Activating Factor of $5\times10^{-9}M$ and $5\times10^{-8}M$ concentration was added.

Then, $IC_{50}$, 50% of the inhibition concentration, of derivatives was searched.

TABLE 2

Comparison of platelet aggregation inhibiting effect of rabbit by PAF.

| Compound | $IC_{50}$ (M) |
| --- | --- |
| Ginkgolide B | $4.27 \times 10^{-7}$ |
| Ginkgolide A | $1.75 \times 10^{-6}$ |
| formula (I-a) | $2.64 \times 10^{-6}$ |
| formula (I-b) | $1.30 \times 10^{-5}$ |
| formula (II) | $1.05 \times 10^{-6}$ |
| formula (IV) | $4.95 \times 10^{-6}$ |
| formula (III) | $6.98 \times 10^{-6}$ |
| formula (III-a) | $7.63 \times 10^{-6}$ |

By the results of the above test, the compound of the formula (I-a), (II), (III), and (IV) among the new derivative compounds were low than the Ginkgolide B in its activity, but they were similar or superior platelet aggregation inhibiting effect to the Ginkgolide A. So it will give us information for development of the new ginkgolide derivatives, if it is researched the activity relationship.

What is claimed is:

1. A new Ginkgolide B derivative of the formula (I) as below

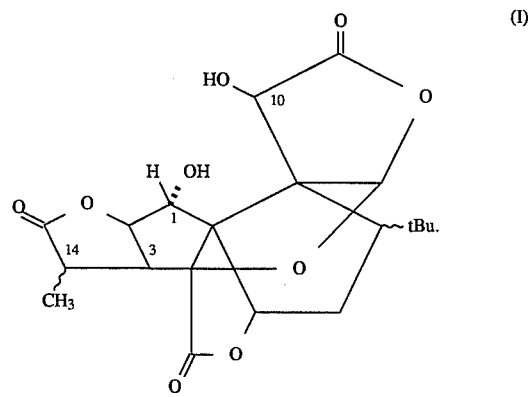

2. A new Ginkgolide B derivative having platelet aggregation inhibiting effect of the formula (II) as below

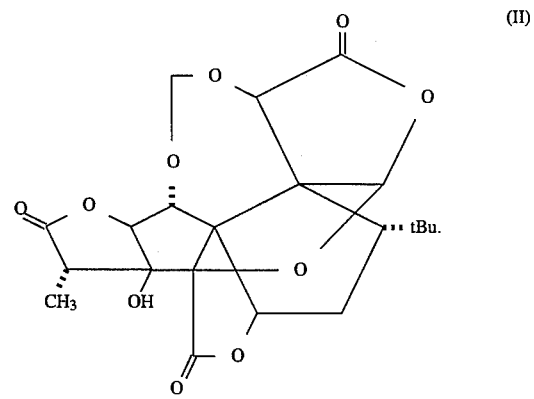

3. A new Ginkgolide B derivative of the formula (III) or (IV) as below
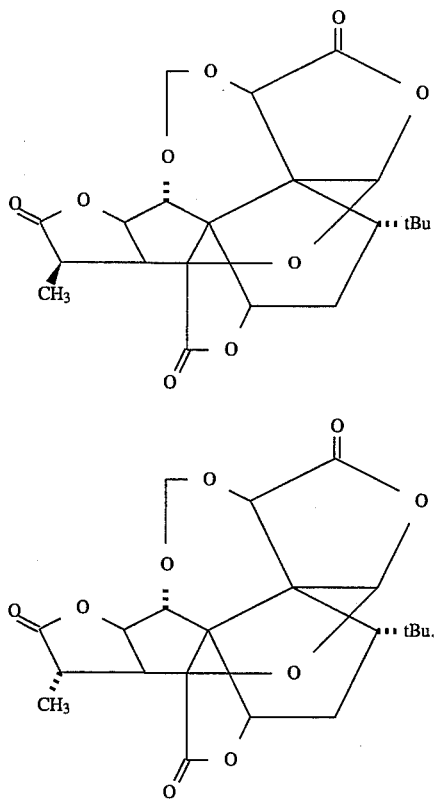
4. PAF-antagonistic agent containing one or more new Ginkgolide B derivative of the formula (I), (II), (III), or (IV) as below
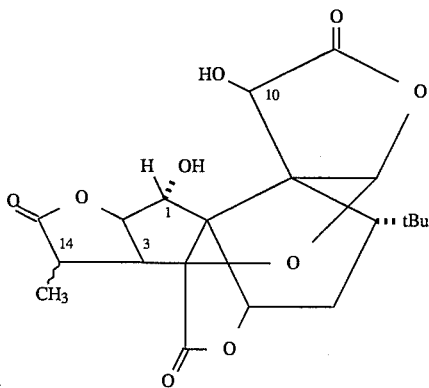
-continued
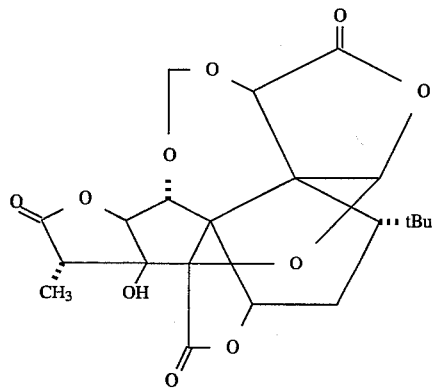
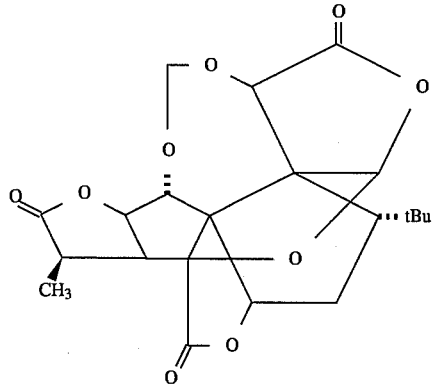
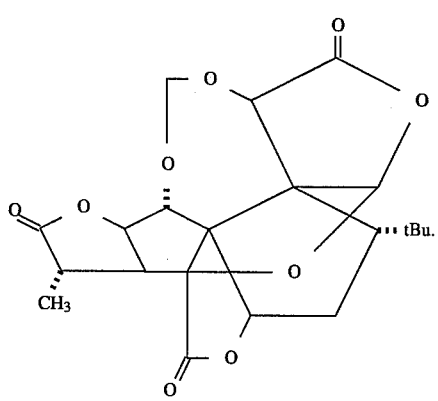
5. A process for preparing the ginkgolide derivatives which is characterized by separating as follows:

the cyclic compounds, substituted ginkgolide derivatives of the formula (II) as below, are obtained by reacting the Ginkgolide B and C mixture that having the hydroxy group in 1- and 10-carbon with aldehyde or ketone in acid solvent, then the unreacted ginkgolides are separated from the reacted ginkgolides, the compounds of the formula (III) and (IV) are obtained from the formula (II), and the compound of the formula (I) is obtained by hydrolysis the compound of formula (III) and (IV) in acidic aqueous solution

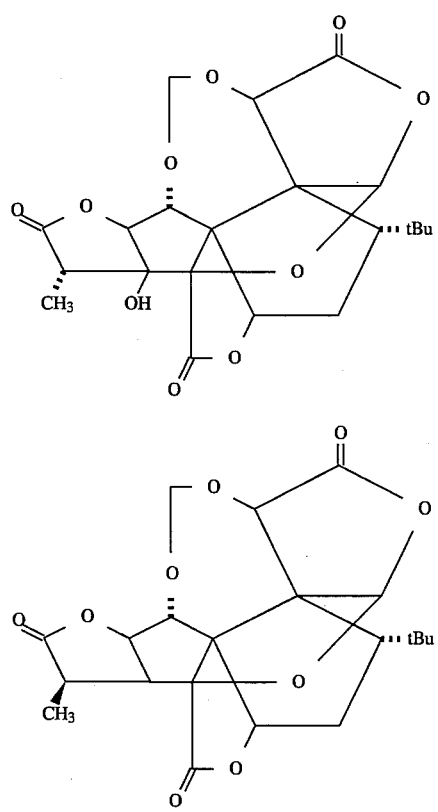

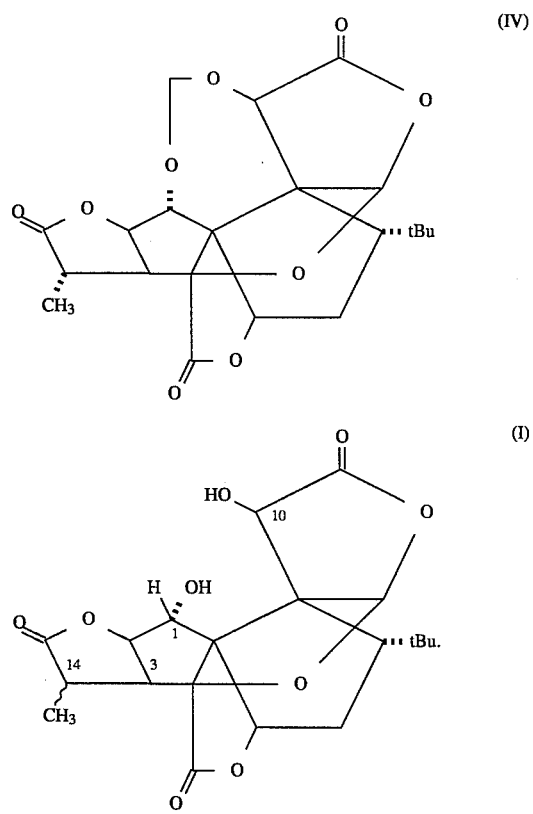

6. The process according to claim 5, wherein the convention to the above formula (II) comprises dissolving the ginkgolide mixture in solution mixed acetic acid with sulfuric acid and adding an excess of formaldehyde or p-formaldehyde.

* * * * *